United States Patent [19]
Von Teichert

[11] Patent Number: 5,897,538
[45] Date of Patent: Apr. 27, 1999

[54] LEAK PREVENTION FITTING FOR INFUSION SET

[76] Inventor: Joseph M. Von Teichert, 1020 N. Laurel Ave., Apt. #2, West Hollywood, Calif. 90046-6029

[21] Appl. No.: 08/898,529

[22] Filed: Jul. 22, 1997

[51] Int. Cl.$^6$ .................................................. A61M 25/00
[52] U.S. Cl. ........................... 604/283; 604/248; 604/256
[58] Field of Search ................................... 604/283, 284, 604/246, 247, 248, 236, 270

[56] References Cited

U.S. PATENT DOCUMENTS

| | | | |
|---|---|---|---|
| 4,661,110 | 4/1987 | Fortier et al. | 604/256 |
| 4,874,365 | 10/1989 | Frederick | 604/270 X |
| 5,074,334 | 12/1991 | Onodera | 604/248 X |
| 5,329,921 | 7/1994 | Socaris et al. | 604/248 |
| 5,382,242 | 1/1995 | Horton et al. | 604/283 |
| 5,472,432 | 12/1995 | Martin | 604/248 |
| 5,578,016 | 11/1996 | Zinger | 604/236 X |
| 5,591,128 | 1/1997 | Sithole | 604/284 X |

*Primary Examiner*—John D. Yasko
*Attorney, Agent, or Firm*—Beehler & Pavitt

[57] ABSTRACT

An improved infusion set of the type including a length of flexible tubing with a hollow needle or catheter projecting from a first end and a connection fitting attached to a second. The fitting is a hollow generally "Y"-shaped tubular body with a first opening connected to the first end of the tubing. Second opening and the third openings, communicating through an orifice, accept a standard tapered fitting. The improvement includes a valving element formed as a standard tapered fitting removably and rotatably fitted to the second opening. The valving element permits or blocks communication between the third opening and the first opening and may removably seal the second opening. The valving element includes a tapered tube with a narrower first end, a wider second end, an inner surface and an outer surface and a transverse opening penetrating both surfaces. This opening is positioned to align with the orifice when the valving element is installed in the second opening and is rotated to a first position. The tapered tube is adapted to seal the orifice in the first tubular section when the valving element is rotated to a second position. The first end of the tapered tube communicates with the first tubular section of the body. The second end of the tapered tube is closed with a permeable self-sealing membrane adapted for use with cannular needles. The invention includes a tapered plug for the third opening and a cap to cover the valving element to preserve sterility.

5 Claims, 5 Drawing Sheets

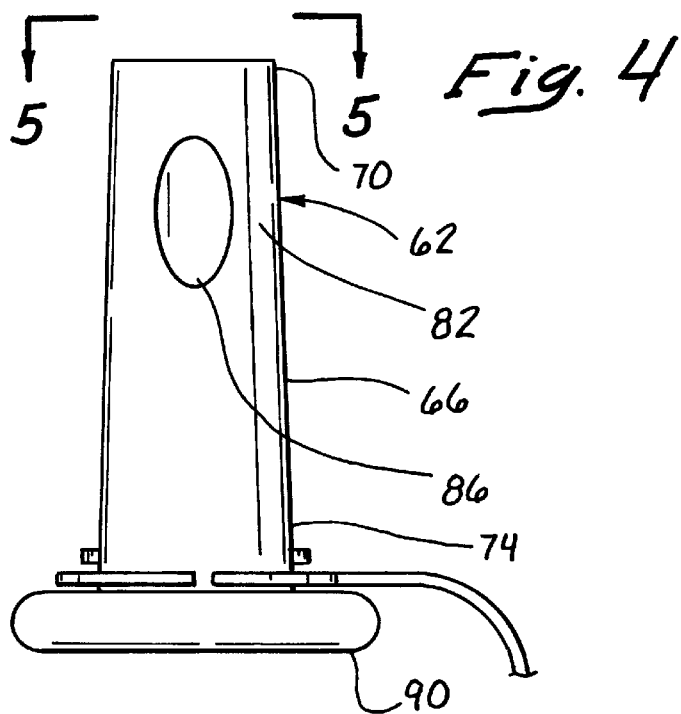
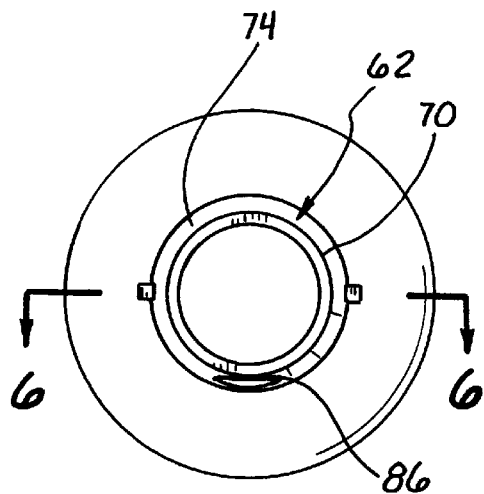
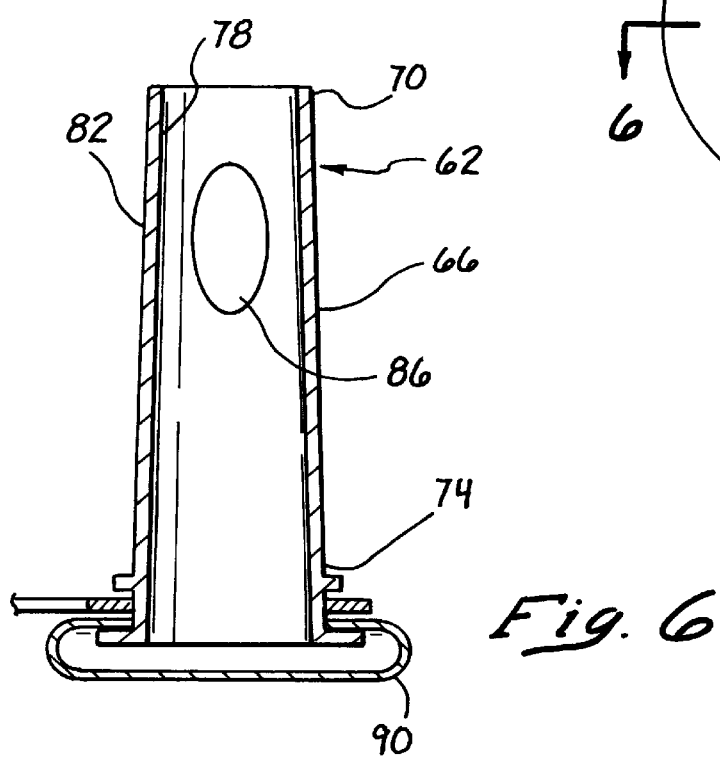

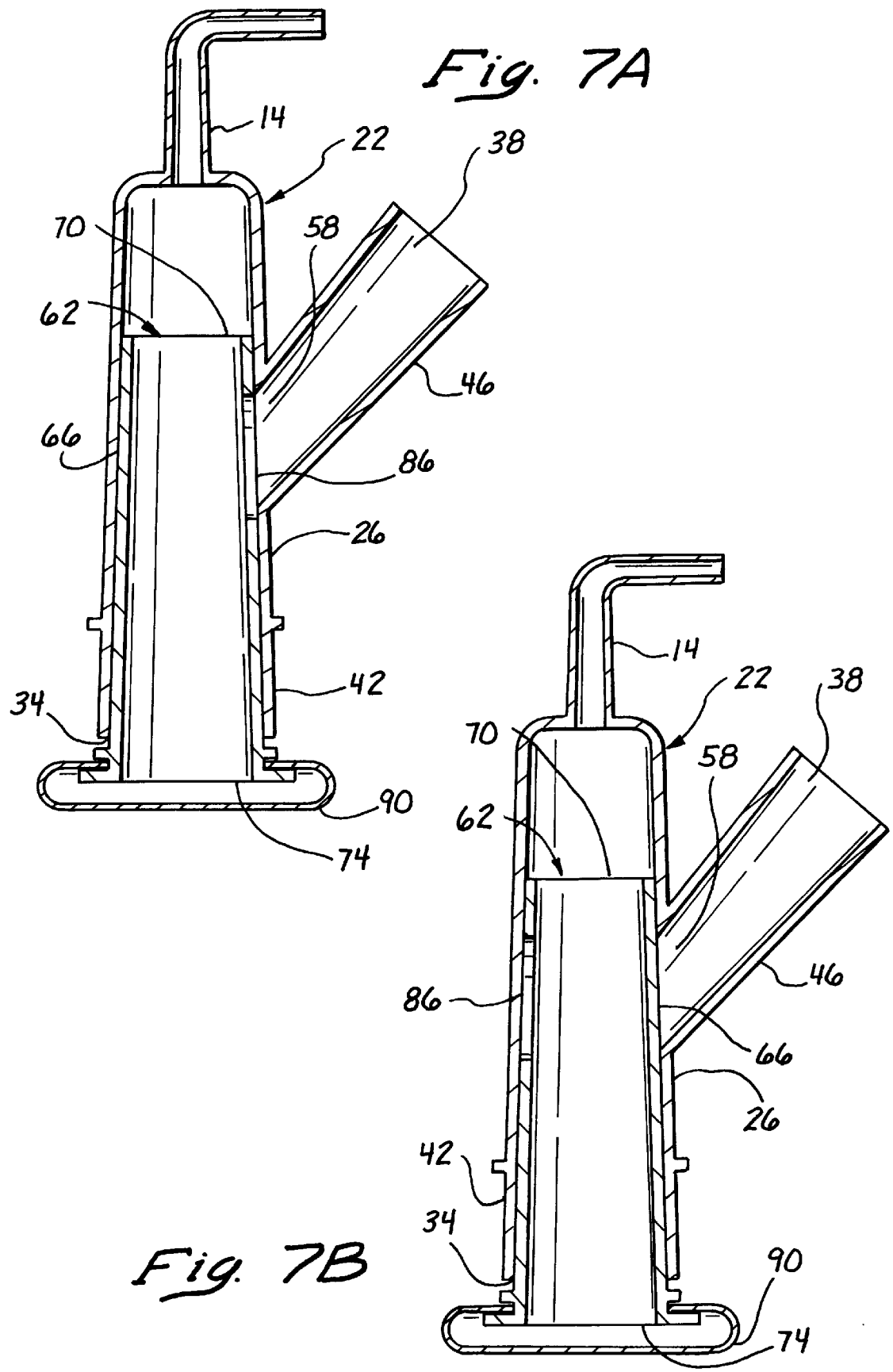

LEAK PREVENTION FITTING FOR INFUSION SET

DISCLOSURE DOCUMENT

The following application relates to an invention conceived on or before Mar. 13, 1996 as established by Disclosure Document No. 394233 filed in the U.S. Patent and Trademark Office on that date. This document is hereby incorporated by reference.

1. Field of the Invention

This invention relates to a medical device, sometimes referred to as an infusion set, used to make a vascular puncture into a patient's blood vessel, and to then remove blood or administer solutions to the patient. More particularly, the invention involves a fitting attached to a infusion tube having special features to minimize leakage of fluids from the fitting and provide positive control of fluids through the infusion tube.

BACKGROUND OF THE INVENTION

2. Description of the Prior Art

The usefulness of infusion sets for administering medical liquids has long been recognized. U.S. Pat. No. 3,670,727 issued to Reiterman in 1972 and U.S. Pat. No. 4,324,236 issued to Gordon in 1982 are typical examples. These sets include an intravenous needle or catheter connected to one end of a flexible tube. The tube is connected by means of an adapter at its other end to a medical liquid source. In many medical situations it is useful to have the adapter include a "Y" fitting to allow connection of the infusion set to alternative sources of medical liquids or to permit the drawing of blood from the patient without an additional puncture.

With the rise of HIV and other infectious diseases, concern, amongst hospital personnel handling blood and other bodily fluids, regarding control and containment of these fluids has increased substantially. An infusion set, typified by the present invention, is often used to first draw a blood sample from the patient, and then to infuse the patient with some type of solution. In the usual sequence of events blood is drawn through one side of the "Y" connector while the other side of the connector is capped with a sterile protective cover. An external clamp is then applied to the flexible tubing to shut off the flow of blood to the connector. The solution source is then connected to the other side of the connector and the clamp is then removed from the flexible tube and the solution flows into the patient.

Using the above scenario, opportunity exists for blood to leak out of the "Y" connector after the blood drawing device is removed. In addition, attachment of the small external clamp to the flexible tubing is difficult to perform quickly and a certain degree of care is required to insure that the clamp is firmly in place.

It is an objective of the present invention to provide a means to prevent leakage of blood or other fluids from the infusion set. It is a further objective of the invention to positively control flow through the flexible tubing of the infusion set from either branch of a "Y" connector. It is another objective of the invention to permit entry of a needle into one branch of the "Y" connector without addition of any other fittings or adapters. It is yet another objective of the invention to provide a means to maintain the connections to the infusion set in sterile condition prior to use.

SUMMARY OF THE INVENTION

The present invention successfully obtains all of the foregoing objectives where prior art devices have failed to adequately meet one or more of the above described objectives or desirable features.

A first embodiment of the present invention is an improved infusion set of the type including a length of flexible tubing having a first end and a second end with a hollow needle or catheter projecting from the first end and a connection fitting in communication with the second end.

In this embodiment the fitting has a hollow generally "Y"-shaped tubular body with a first opening in communication with the second end of the flexible tubing, a second opening, and a third opening. The second opening and the third opening are adapted to accept a standard tapered fitting.

The improvement of the present invention includes a valving element adapted to removably and rotatably fit the second opening. The valving element permits or blocks communication between the third opening and the first opening and is adapted to removably seal the second opening.

Another, preferred embodiment of the invention, is an improved infusion set of the type including a length of flexible tubing having a first end and a second end with a hollow needle or catheter projecting from the first end and a connection fitting in communication with the second end.

In this embodiment the fitting has a hollow generally "Y"-shaped tubular body with a first opening connected to the second end of the flexible tubing, a second opening, and a third opening. The first opening and the second opening are at opposite ends of an essentially straight first tubular section of the body. The third opening is at the end of a second tubular section of the body which is attached at an acute angle to a vertical axis of the first tubular section. The second tubular section communicates with the first tubular section at an orifice. The second opening and the third opening are adapted to accept a standard tapered fitting.

The improved infusion set includes a valving element, in the form of a standard tapered fitting, adapted to removably and rotatably fit the second opening. The valving element permits or blocks communication between the third opening and the first opening of the fitting and the valving element is adapted to removably seal the second opening.

In a variant of this embodiment of the present invention the valving element includes a tapered tube having a narrower first end, a wider second end, an inner surface and an outer surface. The tapered tube includes a transverse opening penetrating from the outer surface to the inner surface. This opening is positioned to align with the orifice when the valving element is installed in the second opening and is rotated to a first position.

The tapered tube is adapted to seal the orifice in the first tubular section when the valving element is rotated to a second position. The first end of the tapered tube communicates with the first tubular section of the body. The second end of the tapered tube is closed with a permeable self-sealing membrane adapted for use with cannular needles.

In another variant of this embodiment, the improved infusion set also includes a flexible bracket for attaching the valving element to the fitting. The bracket includes a first end rotatably mounted to the first tubular section of the fitting adjacent the second opening, a flexible connecting band, and a second end rotatably mounted to the valving element adjacent the wider second end of the tapered tube. The bracket is adapted to permit the valving element to be easily inserted into the second opening in the fitting.

A further variant of this embodiment of the present invention includes a tapered plug adapted to removably seal the third opening to preserve sterility of the interior of the fitting. This variant also includes a cap having a tapered interior adapted to removably cover the tapered portion of the valving element to preserve its sterility.

In use, the infusion set is received in a sterile wrapper. The infusion set is removed from the sterile wrapper and the catheter is inserted into a patient's vein and taped in place. Typically, blood samples are next drawn through the second opening of the fitting. Next the cap is removed from valving element and the valving element is inserted into the second opening of the fitting. The valving element is rotated to a first position so that the transverse opening aligns with orifice between the first tubular section and the second tubular section of the fitting. The tapered plug is then removed from the third opening of fitting and an infusion source is connected to the third opening using a standard tapered fitting connector.

If it is desired to shut off the flow from the infusion source, the valving element is rotated to a second position, causing the tapered tube to removably seal the orifice, thereby preventing any communication between the third opening of the fitting and the first opening. If desired, additional blood may be drawn or other injections introduced through the permeable membrane by means of a cannular needle or syringe. By maintaining the valving element in the second opening of the fitting, leakage of blood from the infusion set is minimized.

DESCRIPTION OF THE DRAWINGS

In the accompanying drawings:

FIG. 4 is a side view of the valving element adapted to fit the connection fitting shown in FIG. 2;

FIG. 5 is a plan view of the valving element shown in FIG. 4;

FIG. 6 is a cross-sectional view of the valving element shown in FIG. 4 taken along the line 6—6;

FIG. 7a is an enlarged cross-sectional view of the connection fitting of the FIG. 1 embodiment taken along the line 7a—7a with an enlarged cross-sectional view of the valving element of the FIG. 1 embodiment taken along the line 7a'—7a' inserted in the second opening;

FIG. 7b is an enlarged cross-sectional view of the connection fitting of the FIG. 1 embodiment taken along the line 7a—7a with an enlarged cross-sectional view of the valving element of the FIG. 1 embodiment taken along the line 7a"–7a" inserted in the second opening;

DESCRIPTION OF THE PREFERRED EMBODIMENT

Figure 1:
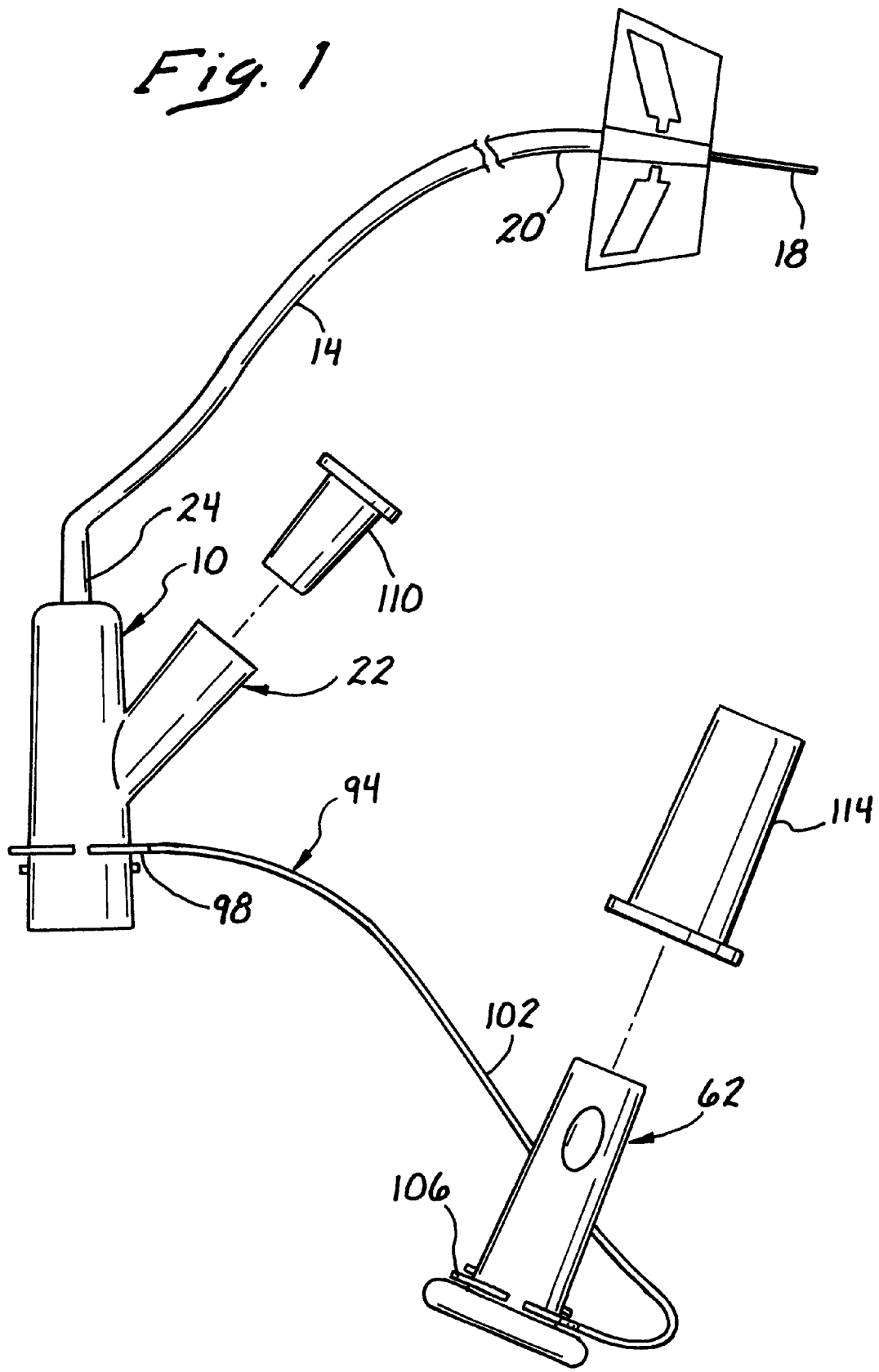
FIG. 1 is a side view of the preferred embodiment of the invention.

The preferred embodiment of the invention, as illustrated in FIG. 1, is an improved infusion set 10 of the type which includes a length of flexible tubing 14 having a first end 20 and a second end 24 with a hollow needle or catheter 18 projecting from the first end 20 and a connection fitting 22 in communication with the second end 24.

Figure 2:
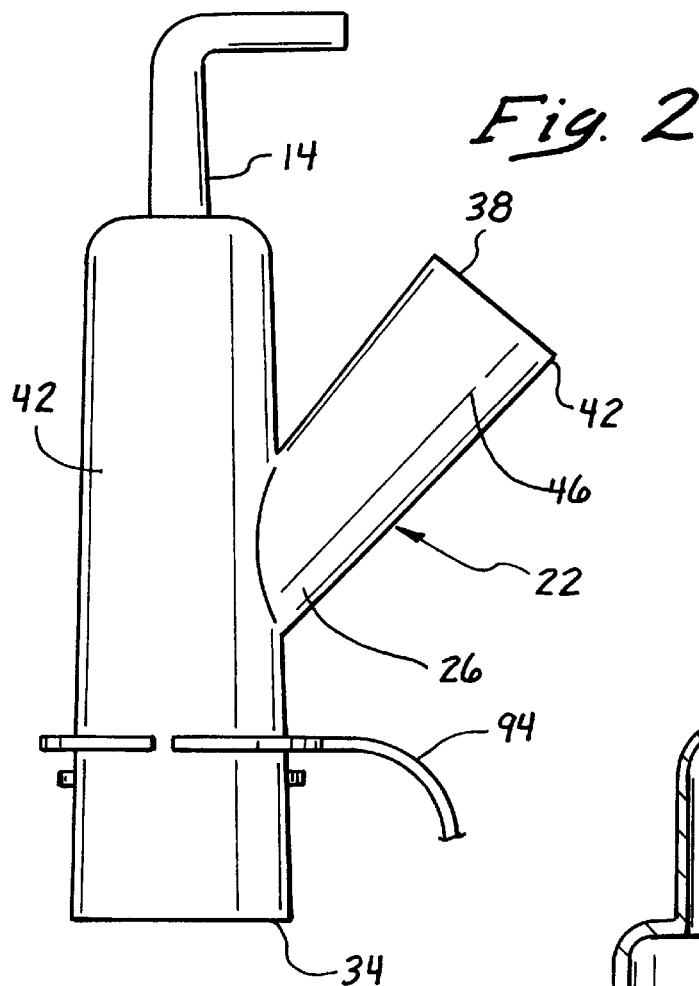
FIG. 2 is an enlarged side view of the connection fitting of the FIG. 1 embodiment.
Figure 3:
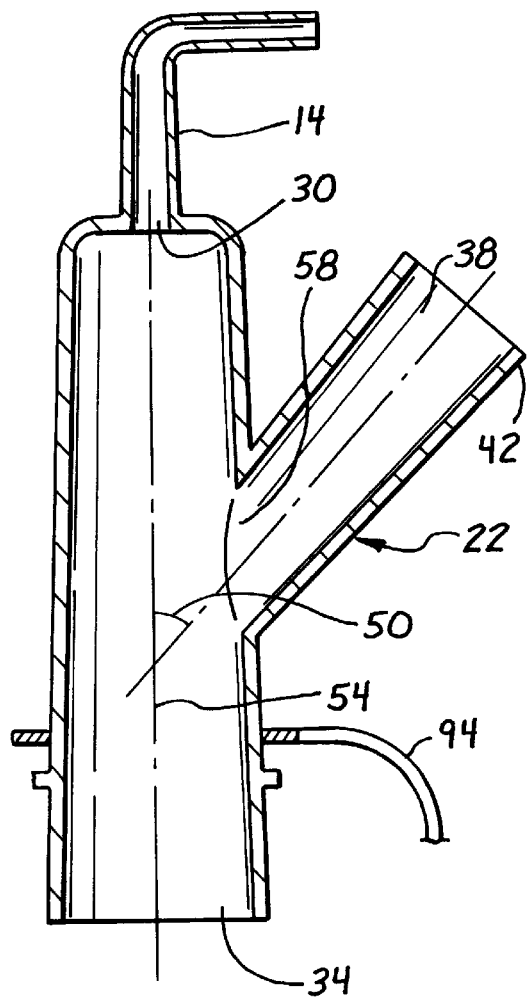
FIG. 3 is a cross-sectional view of the connection fitting shown in FIG. 2 taken along the line 3—3.

FIGS. 2 and 3 illustrate the fitting 22 which has a hollow generally "Y"-shaped tubular body 26 with a first opening 30 in communication with the second end of the flexible tubing 14, a second opening 34, and a third opening 38. The first opening 30 and the second opening 34 are at opposite ends of an essentially straight first tubular section 42 of the body 26. The third opening 38 is at the end 42 of a second tubular section 46 of the body 26 which is attached at an acute angle 50 to a vertical axis 54 of the first tubular section 42. The second tubular section 46 communicates with the first tubular section 42 through an orifice 58. The second opening 34 and the third opening 38 are each adapted to accept a standard tapered fitting.

FIGS. 4–6 and FIGS. 7a and 7b illustrate a valving element 62 adapted to removably and rotatably fit the second opening 34 of the fitting 22 of the improved infusion set 10. The valving element 62 controls the communication between the third opening 38 and the first opening 30 of the fitting 22. The valving element 62 is adapted to removably seal the second opening 34 of the fitting 22.

The valving element 62 includes a tapered tube 66 having a narrower first end 70, a wider second end 74, an inner surface 78 and an outer surface 82. The tapered tube 66 includes a transverse opening 86 penetrating from the outer surface 82 to the inner surface 78.

FIG. 7a illustrates the alignment of opening 86 with the orifice 58 when the valving element 62 is installed in the second opening 34 and is rotated to a first position. FIG. 7b shows tapered tube 66 sealing the orifice 58 in the first tubular section 42 when the valving element 62 is rotated to a second position. The first end 70 of the tapered tube 66 communicates with the first tubular section 42 of the body 26. The second end 74 of the tapered tube 66 is closed with a permeable self-sealing membrane 90 adapted for use with cannular needles (not shown).

Figure 10:
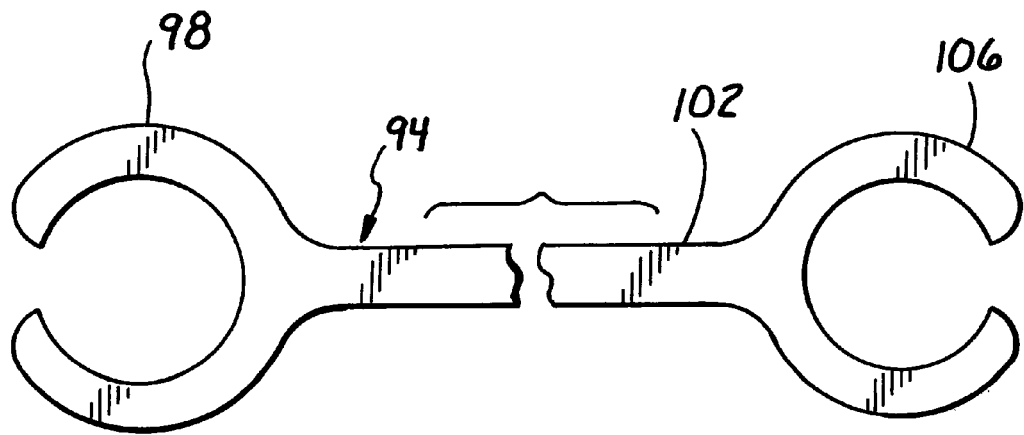
FIG. 10 is a plan view of a flexible bracket for connecting the connection fitting shown in FIG. 2 to the valving element shown in FIG. 4.

FIGS. 1 and 10 illustrate a flexible bracket 94 for attaching the valving element 62 to the fitting 22. The bracket 94 includes a first end 98 rotatably mounted to the first tubular section 42 of the fitting 22 adjacent the second opening 34, a flexible connecting band 102, and a second end 106 rotatably mounted to the valving element 62 adjacent the wider second end 74 of the tapered tube 66. The bracket 94 is adapted to permit the valving element 62 to be easily inserted into the second opening 34 in the fitting 22.

Figure 8:
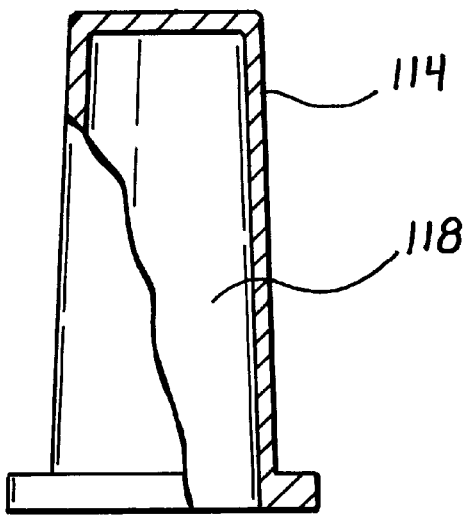
FIG. 8 is a side view of a cap for protecting the sterility of the valving element shown in FIG. 4.
Figure 9:
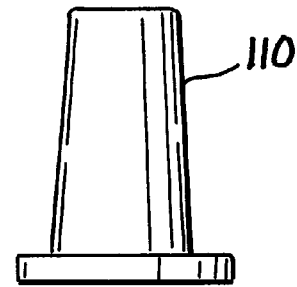
FIG. 9 is a partial cross-sectional side view of a plug for protecting the sterility of the third opening of the connection fitting shown in FIG. 2.

FIG. 9 illustrates a tapered plug 110 adapted to removably seal the third opening 38 to preserve sterility of the interior of the fitting 22. FIG. 8 shows a cap 114 having a tapered interior 118 adapted to removably cover the tapered tube 66 of the valving element 62 to preserve its sterility.

In use, the infusion set as illustrated in FIG. 1 is received in a sterile wrapper (not shown). The infusion set 10 is removed from the sterile wrapper and the catheter 18 is inserted into a patient's vein and taped in place. Typically, blood samples are next drawn through the second opening 34 of fitting 22. Next cap 114, as illustrated in FIGS. 1 and 8, is removed from valving element 62 and the valving element is inserted into the second opening 34 of fitting 22. As illustrated in FIG. 7a, valving element 62 is rotated to a first position so that transverse opening 86 aligns with orifice 58 between the first tubular section 42 and the second tubular section 46 of fitting 22. Tapered plug 110, as illustrated in FIGS. 1 and 9, is removed from the third opening 38 of fitting 22 and an infusion source (not shown) is connected to the third opening 38 with a standard tapered fitting connection.

If it is desired to shut off the flow from the infusion source, valving element 62 is rotated to a second position, as illustrated in FIG. 7b, causing tapered tube 66 to removably seal orifice 58, thereby preventing any communication between the third opening 38 and the first opening 30. If desired, additional blood may be drawn or other injections introduced through permeable membrane 90 by means of a cannular needle or syringe (not shown). By maintaining valving element 62 in the second opening 34 of fitting 22, leakage of blood from the infusion set is minimized.

The foregoing detailed disclosure is intended as merely exemplary, and not to limit the scope of the invention—which scope is to be determined by reference to the appended claims.

I claim:

1. An improved infusion set of the type including a length of flexible tubing having a first end and a second end with a hollow needle or catheter projecting from the first end and a connection fitting in communication with the second end, the improvement comprising:

the fitting being formed as a hollow generally "Y"-shaped tubular body with a first opening being in communication with the second end of the tubing, a second opening, and a third opening;

the second opening and the third opening adapted to accept a standard tapered fitting;

a valving element, said valving element adapted to removably and rotatably fit the second opening;

said valving element permitting or blocking communication between the third opening and the first opening; and the valving element removably sealing the second opening.

2. An improved infusion set of the type including a length of flexible tubing having a first end and a second end with a hollow needle or catheter projecting from the first end and a connection fitting in communication with the second end, the improvement comprising:

the fitting being formed as a hollow generally "Y"-shaped tubular body with a first opening being in communication with the second end of the tubing, a second opening, and a third opening;

the first opening and the second opening being at opposite ends of an essentially straight first tubular section of the body;

the third opening being at an end of a second tubular section of the body attached at an acute angle to a vertical axis of the first tubular section and communicating with the first tubular section at an orifice;

the second opening and said third opening adapted to accept a standard tapered fitting;

a valving element, said valving element being in the form of a standard tapered fitting and adapted to removably and rotatably fit the second opening;

said valving element permitting or blocking communication between the third opening and the first opening; and said valving element removably sealing said second opening.

3. The improved infusion set of claim 2, wherein said valving element further comprises:

a tapered tube having a narrower first end, a wider second end, an inner surface and an outer surface;

the tapered tube including a transverse opening penetrating from the outer surface to the inner surface;

said transverse opening being positioned to align with the orifice when the valving element is installed in the second opening and is rotated to a first position, thereby permitting communication between the first opening and the third opening;

the valving element being adapted to seal the orifice between the first tubular section and the second tubular section when the valving element is rotated to a second position, thereby blocking communication between the first opening and the third opening;

the first end of the tapered tube communicating with the first tubular section of the body; and the second end of the tapered tube being closed with a permeable self-sealing membrane adapted for use with cannular needles.

4. The improved infusion set of claim 3, further comprising:

a flexible bracket for attaching the valving element to the fitting;

said bracket including a first end rotatably mounted to the first tubular section of the fitting adjacent the second opening, a flexible connecting band, and a second end rotatably mounted to the valving element adjacent the wider second end of the tapered tube; and the bracket adapted to permit the valving element to be easily inserted into the second opening in the fitting.

5. The improved infusion set of claim 2, further comprising:

a tapered plug adapted to removably seal the third opening to preserve sterility; and a cap having a tapered interior adapted to removably cover the valving element to preserve sterility.

* * * * *